United States Statutory Invention Registration [19]

[11] Reg. Number: H692

Matthewson et al. [43] Published: Oct. 3, 1989

[54] PEST CONTROL

[75] Inventors: Michael D. Matthewson; Gerald G. Blackman, both of Berkhamsted, England

[73] Assignee: Burroughs Wellcome Co., Research Triangle Park, N.C.

[21] Appl. No.: 151,237

[22] Filed: Oct. 27, 1987

Related U.S. Application Data

[60] Continuation of Ser. No. 365,532, Apr. 5, 1982, which is a division of Ser. No. 213,930, Dec. 8, 1980, abandoned, which is a continuation of Ser. No. 29,337, Apr. 12, 1979, abandoned, which is a continuation of Ser. No. 863,736, Dec. 23, 1977, abandoned.

[51] Int. Cl.[4] ..... A61K 31/275

[52] U.S. Cl. ..... 514/52; 424/DIG. 10

*Primary Examiner*—John F. Terapane
*Assistant Examiner*—J. E. Thomas
*Attorney, Agent, or Firm*—Donald Brown

[57] ABSTRACT

A method of treating an animal for the prevention or control of infestation by insects of the Order Diptera which comprises application to the animal of a compound of formula

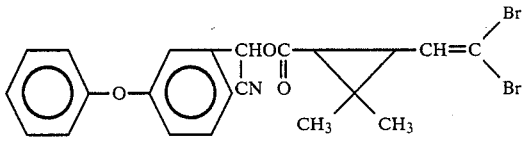

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PEST CONTROL

This is a continuation of co-pending application Ser. No. 365,532, filed on Apr. 5, 1982, which is a divisional of Ser. No. 213,930, filed on Dec. 8, 1980, now abandoned, which is a continuation of Ser. No. 29,337, filed on Apr. 12, 1979, now abandoned, which is a continuation of Ser. No. 863,736, filed on Dec. 23, 1977, now abandoned.

This invention concerns the new use of known compounds and formulations containing them.

Flies of the Order Diptera are a source of concern in animal husbandry as troublesome pests of many domestic animals. Apart from infesting animal wounds with eggs which mature in the flesh, they transmit a variety of infectious diseases by biting the animals, and can cause weight loss and decrease in milk yield.

A variety of insecticides have been shown to be active against such flies, and some have found commercial application in preventing or limiting irritation of the animals. Such preparations have included DDT, pyrethrins, methoxychlor and diazinon, but all known remedies have at least one of the drawbacks of little or no repellant action on the flies, low insecticidal activity, and poor residual effects. A repellant effect of an insecticide is of particular importance in minimising fly worry or preventing the fly from attaching itself to the host thus decreasing the annoyance to the animal and the risk of infection.

Pyrethrins in particular are recognized to have little commercial potential as repellants for nuisance flies and have further found little commercial application in the control of other arthropod ectoparasites of animals such as ticks, lice, mites and keds. Amongst the synthetic pyrethroid analogues of pyrethrins the compound bioresmethrin (2-benzyl-4-furylmethyl d-trans chrysanthemate) is known to be outstanding as a killing agent as measured by for example results obtained from topical application of the compound to adult houseflies (*Musca domestica*) but has been found to have only limited knock-down activity against these flies compared with that of pyrethrins.

The compound permethrin, 3-phenoxybenzyl-2,2-dimethyl-3-(2,2-dichlorovinyl)cyclopropane-1-carboxylate is known from Belgian Patent No. 818820 to provide a protective effect for livestock against attack by insects of the Order Diptera and that this effect includes a repellant effect, an insecticidal effect and a residual effect.

α-Cyano-3-phenoxybenzyl-2,2-dimethyl-3-(2,2-dibromovinyl)cyclopropane-1-carboxylate, and its optical and geometrical isomers, (hereinafter referred to as the compounds of formula (I) are known (from U.K. Patent Nos. 1,413,491 and 1,448,228) to have insecticidal activity against a variety of insects including *Musca domestica.*

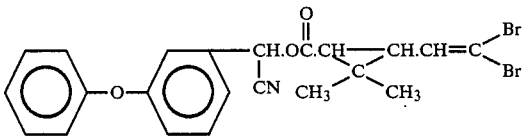

(I)

The structural formula (I) is intended to cover all the geometric and optical isomers of the compound including the (+)-cis-isomer, the (+)-trans-isomer, the (±)-trans-isomer, the (±)-cis-isomer and the (±)-cis-trans-isomer (the sterochemistry referring to that of the cyclopropane rings). Moreover the alcohol moiety of the ester of formula (I) may be selected from the (−)-isomer, the (+)-isomer and the (±)-isomer. The preferred isomer is (−)-α-cyano-3-phenoxybenxyl-(+)-cis-2,2-dimethyl-3-(2,2-dibromovinyl)cyclopropane-1-carboxylate.

It has now been found that the compounds of formula (I) provide animals with a remarkable protective effect against attack by insects of the Order Diptera, and that this effect includes a high repellant effect, an excellent insecticidal effect, and long residual protection of the animals against infestation when the compounds of formula (I) are used at substantially lower doses than have hitherto been used for permethrin and for pyrethrins. In particular the compounds are very effective in protecting cattle against the stable fly (*Stomoxys calcitrans*) the horn fly (*Haematobia irritans*) and the buffalo fly (*Lyperosia exigua*).

The compounds of formula (I) may be used in the protection of a variety of animals against Diptera, which include cattle, horses, sheep and other ungulates, chickens and dogs.

Pests which may be controlled by the use of compounds of formula (I) include Simulidae (e.g. *Simulium sp.*), Tabanidae (e.g. *Tabanus sp.*), Muscidae (e.g. *Stomoxys calcitrans, Glossina sp., Lyperosia sp., Haemathobia sp.*, and *Hydrotaea sp.*), Caliphoridae (e.g. *Lucilia sp., Chrysomyia sp., Calliphora sp.* and *Callitroga sp.*) and Oestridae (e.g. *Hypoderma bovis, H. lineatum, Oestrus Ovis* and *Dermatobia hominis*).

The compounds of formula (I) may be used for such purposes by application of the compounds themselves or in a diluted form in known fashion as a dip, spray, foam, dust, aqueous suspension, paste, gel, shampoo, grease, aerosol, impregnated article or pour-on formulation. Dip concentrations are not applied per se, but are diluted with water and the animals immersed in a dipping bath containing the dip wash. Sprays may be applied by hand or by means of a spray race or arch. The animal may be saturated with the spray by means of high volume application or superficially coated with the spray by means of light or ultra low volume application. Aqueous suspensions may be applied to the animal in the same manner as sprays. Dusts may be distributed over the animals by means of a powder applicator or incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of relatively low volume on to the backs of animals such that all or most of the liquid is retained on the animals.

The compounds of formula (I) may be formulated either as formulations ready for use on the animals or as formulations requiring further dilution prior to application, but both types of formulations comprise a compound of formula (I) in intimate admixture with one or more carriers or diluents. The carriers may be liquid, solid or gaseous or comprise mixtures of such substances, and the compound of formula (I) may be present in a concentration of from 0.025 to 99% w/v depending upon whether the formulation requires further dilution.

Dusts may be prepared by intimate admixture of the chosen compound with a powered solid inert carrier for example suitable clays, kaolin, talc, mica, starch and diatomaceous earths.

Sprays of a compound of formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present in wide limits but preferably in an amount of from 20 to 60% w/v of the composition and may be selected from kerosene, ketones, alkanols, xylene, aromatic naphtha, and other solvents known in the formulating art. The concentration of emulsifiers may be varied within wide limits but preferably in the range of 5 to 25% w/v and are conveniently non-ionic surface active agents including polyoxyalkylene esters of alkyl phenols and polyoxyethylene derivatives of hexitol anhydrides.

Dip washes may be prepared not only from emulsifiable concentrates but also from wettable powders comprising a compound of formula (I) in intimate admixture with a dispersing agent and one or more surface active agents.

Aqueous suspensions of a compound of formula (I) may comprise a suspension in water together with suspending, stabilizing or other agents. The suspensions may be applied per se or in a diluted form in known fashion.

Greases (or ointments) may be prepared from vegatable oils, synthetic esters of fatty acids or wool fat together with an inert base such as soft paraffin.

A compound of formula (I) is preferably distributed uniformly through the mixture in solution or suspension. Greases may also be made from emulsifiable concentrates by diluting them with an ointment base.

Pastes and shampoos are also semi-solid preparations in which a compound of formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of formula (I) required for treatment.

Aerosol sprays may be prepared as a simple solution of the active ingredient in the aerosol propellant and a co-solvent such as halogenated alkanes and the solvents referred to above, respectively. Pour-on formulations may be made as a solution or suspension of a compound of formula (I) in a liquid medium which also contains a viscous oil to minimize spreading of the formulation on the surface of the animals.

An animal host may be protected against infestation of Dipteran parasites by means of carrying a suitable-moulded, shaped plastic article impregnated with a compound of formula (I). Such articles include impregnated collars, tags, bands, sheets and strips suitably attached to appropriate parts of the body.

The concentration of the compound of formula (I) to be applied to an animal will vary according to the isomer chosen, the nature of the formulation and the likely infestation, but in general 0.001% to 1% w/v of the compound should be present in the applied formulation. For the control of biting flies, a regular application, for example weekly, by standard techniques of a solution or emulsion of 0.001 to 0.1% w/v has been found to provide satisfactory control. It will be understood that the amount of the compound deposited on an animal will vary according to the method of application, the size of the animal, the concentration of the compound in the applied formulation and the nature of the formulation.

Dusts, greases, pastes and aerosol formulations are usually applied at concentrations of 0.001 to 1.0% w/v of a compound of formula (I) in the applied formulation.

It will be appreciated from the foregoing that what we will claim may comprise any novel feature described herein, principally and not exclusively, for example:

(a) A method of treating an animal for the prevention or control of infestation of insects of the Order Diptera which comprises application to the animal of a non-toxic infestation prevention or control effective amount of α-cyano-3-phenoxybenzyl-2,2-dimethyl-3-(2,2-dibromovinyl)cyclopropane-1-carboxylate or of a formulation comprising said compound in intimate admixture with a carrier or diluent therefor.

The following Examples illustrate the present invention and the manner in which it may be carried out but should not be construed as in any way constituting a limitation thereof. In the Examples, Decamethrin refers to (−)-α-cyano-3-phenoxybenzyl-(+)-cis-2,2-dimethyl-3-(2,2-dibromovinyl) cyclopropane-1-carboxylate.

EXAMPLE 1

Groups of mice were sprayed with a range of washes, at differing concentrations of Decamethrin (each wash comprising Decamethrin dissolved in an organic solvent and emulsifiers and emulsified in water), and the mice allowed to clean themselves and dry. After a period of 4 hours the mice were anaesthetised and strapped over gauze boxes containing adult *Stomoxys calcitrans* previously starved for 24 hours, and the host and flies allowed to remain in contact. After 0.5 hour and flies were anaesthetised, squashed between filter paper and the number having blood in the abdomen counted. The % of repelled flies against the concentration of Decamethrin applied to the mice is plotted and the $RC_{50}$ and $RC_{99}$ values (the concentration of Decamethrin which repels 50% and 99% of the flies respectively) is calculated from the regression line.

For Decamethrin the $RC_{50}$ (%) was 0.0020 and the $RC_{99}$ (%) was 0.02.

EXAMPLE 2

Friesian steers, matched for their susceptibility to *S. calcitrans* were arranged into groups according to susceptibility. Each steer in a group was sprayed at 7 or 14 day intervals with 1 liter of wash containing Decamethrin at a certain concentration; steers of other groups were sprayed with washes of other concentrations. (The washes were prepared by appropriate dilution of a 20% w/v miscible-oil and applied to the animal as a light tip-spray by means of a knapsack sprayer).

Exposures of starved adult *S. calcitrans* were made before and after treatment and the number of flies alighting on each steer during the exposure was counted.

The length of protection afforded was determined by the selection of a value of 67% of the pre-treatment count of *S. calcitrans* as the break-point.

The results are tabulated below:

| Concentration (% w/v) | Treatment Interval days | Days protection (average) |
|---|---|---|
| 0.0125 | 7 | 2 |

-continued

| Concentration (% w/v) | Treatment Interval days | Days protection (average) |
|---|---|---|
| 0.0250 | 7 | 6 |
| 0.0500 | 14 | 9 |
| 0.0750 | 14 | 14 |
| 0.1000 | 14 | 14 |

EXAMPLE 3

Seven sheep were dipped in a wash containing 0.05% w/v of Decamethrin prepared from a 2.5% w/v miscible-oil. At weekly intervals post-treatment portions of the sheeps' fleece were parted and 1 to 2 drops of a fly-attractant were applied. The attractant was prepared by homogenisation of *Lucilia sericata* (N strain) larvae feeding on ox-liver. Glucose and saline solution were added to the homogenate to afford the attractant as a suspension. Seven control undipped sheep were similarly treated with the attractant.

The control and test sheep were then exposed to gravid, female, *Lucilia sericata* (N strain). Six hours later a comparison was made between the number of eggs laid on the dipped as opposed to the undipped sheep by estimating the number of eggs present in each cluster.

If a dipped sheep carried more than two eggs in any cluster protection was not regarded as being obtained.

The results obtained indicated that approximately 13 weeks protection against oviposition by adult *Lucilia sericata* N was afforded by the above treatment.

EXAMPLE 4

| Wettable Powder Formulations | (a) % w/w | (b) % w/w |
|---|---|---|
| Decamethrin | 2.5 | 25.0 |
| Celite 209 | 68.5 | 51.0 |
| Kaolin | 25.0 | 20.0 |
| Perminal BX | 1.0 | 1.0 |
| Dispersol AC | 3.0 | 3.0 |
| | 100.0 | 100.0 |

Celite 209 is an inert carrier.

Perminal BX and Dispersol AC are wetting agents.

EXAMPLE 5

| Miscible-oil Formulations | (a) % w/w | (b) % w/w |
|---|---|---|
| Decamethrin | 2.5 | 19.0 |
| Cyclohexanone | — | 15.0 |
| Esso 200 Solvent | 85.0 | 53.5 |

-continued

| Miscible-oil Formulations | (a) % w/w | (b) % w/w |
|---|---|---|
| Anionic/Non-ionic Emulsifier | 12.5 | 12.5 |
| | 100.00 | 100.00 |

Esso 200 Solvent is a mobile oil which consists of 95% of aromatic hydrocarbons.

EXAMPLE 6

| Pressure-packed Aerosol Formulations | (a) | (b) | (c) | (d) |
|---|---|---|---|---|
| Decamethrin | 0.20 | 0.10 | 0.05 | 0.01 |
| Methylene chloride | 25.00 | 44.90 | 39.95 | |
| Iso-propyl alcohol | 14.80 | — | — | 19.99 |
| Refined Petroleum Solvent | — | 55.00 | 20.00 | — |
| 50/50 Trichlorofluoro methane/dichlorodifluoro methane | 60.00 | — | — | — |
| Butane/Propane mixture | — | — | 40.00 | |
| Water | — | — | — | 40.00 |
| Dimethyl ether | — | — | — | 40.00 |
| | 100.00 | 100.00 | 100.00 | 100.00 |

The butane/propane mixture is chosen so as to have a pressure of 40 pounds per square inch at 21° C.

EXAMPLE 7

| Dusting Powder Formulations | (a) % w/w | (b) % w/w |
|---|---|---|
| Decamethrin | 0.005 | 1.0 |
| Talc | 99.995 | 99.0 |
| | 100.000 | 100.0 |

EXAMPLE 8

| Aqueous Suspensions | (a) % w/w | (b) % w/w |
|---|---|---|
| Decamethrin | 5.0 | 20.0 |
| Aerosol OTB | 0.2 | 0.2 |
| Keltrol | 0.8 | 0.6 |
| Water | 74.0 | 61.2 |
| Glycerol | 20.0 | 15.0 |
| | 100.0 | 100.0 |

Aerosol OTB is a wetting agent.

Keltrol is a thickening/suspending agent.

What we claim is:

1. A method of repelling flies from an animal which comprises depositing on said animal a non-toxic effective fly repellant amount of (−)-α-cyano-3-phenoxybenzyl-(+)-cis-2,2-dimethyl-3-(2,2-dibromovinyl) cyclopropane-1-carboxylate.

* * * * *